(12) United States Patent
Klocke et al.

(10) Patent No.: US 8,390,279 B2
(45) Date of Patent: Mar. 5, 2013

(54) DEGRADATION AND INTEGRITY MEASURING DEVICE FOR ABSORBABLE METAL IMPLANTS

(75) Inventors: Bjoern Klocke, Zurich (CH); Olaf Skerl, Bad Doberan (DE)

(73) Assignee: Biotronik vi Patent AG, Baar (CH)

( * ) Notice: Subject to any disclaimer, the term of this patent is extended or adjusted under 35 U.S.C. 154(b) by 428 days.

(21) Appl. No.: 12/691,329

(22) Filed: Jan. 21, 2010

(65) Prior Publication Data

US 2010/0171492 A1    Jul. 8, 2010

(30) Foreign Application Priority Data

Jan. 30, 2009   (DE) .......................... 10 2009 000 501

(51) Int. Cl.
    *G01N 27/72* (2006.01)
(52) U.S. Cl. .................. 324/228; 324/236; 324/117 H; 600/435; 600/424; 600/431
(58) Field of Classification Search .............. 324/117 H, 324/117 R, 126–127, 228; 600/435
    See application file for complete search history.

(56) References Cited

U.S. PATENT DOCUMENTS

| 5,425,367 | A   | * | 6/1995  | Shapiro et al. ............... 600/424 |
| 5,649,546 | A   |   | 7/1997  | Steinbeck |
| 5,665,103 | A   |   | 9/1997  | Lafontaine et al. |
| 6,493,573 | B1  |   | 12/2002 | Martinelli et al. |
| 7,030,602 | B2  | * | 4/2006  | Khalin et al. ................. 324/127 |
| 7,301,332 | B2  | * | 11/2007 | Govari et al. ............. 324/207.21 |
| 7,397,364 | B2  | * | 7/2008  | Govari ....................... 340/539.12 |
| 2007/0185397 | A1 | * | 8/2007 | Govari et al. ................. 600/424 |
| 2008/0252289 | A1 | * | 10/2008 | Lenglet .......................... 324/253 |

FOREIGN PATENT DOCUMENTS

| DE | 91 07 798.2 U | 11/1991 |
| WO | WO 86/02539 A1 | 5/1986 |
| WO | WO 90/00030 | 1/1990 |
| WO | WO 2006/067664 A2 | 6/2006 |
| WO | WO 2006/122203 A1 | 11/2006 |

OTHER PUBLICATIONS

German Search Report for Priority Document DE 10 2009 000 501.3.

* cited by examiner

*Primary Examiner* — Richard Isla Rodas
(74) *Attorney, Agent, or Firm* — Biotech Beach Law Group PC

(57) ABSTRACT

The present invention relates to a measuring device including a sensor catheter, an evaluation unit, and means for receiving a magnetic field and converting the magnetic field to an electrical measurement signal which are situated in the sensor catheter and connected to the evaluation unit. The evaluation unit is designed to evaluate the electrical measurement signal.

12 Claims, 3 Drawing Sheets

DEGRADATION AND INTEGRITY MEASURING DEVICE FOR ABSORBABLE METAL IMPLANTS

CROSS REFERENCE TO RELATED APPLICATIONS

This invention claims benefit of priority to Germany patent application serial number DE 10 2009 000 501.3, filed on Jan. 30, 2009; the contents of which is herein incorporated by reference in its entirety.

FIELD OF THE INVENTION

The invention relates to a measuring device and the use of this measuring device.

BACKGROUND OF THE INVENTION

Absorbable metallic implants, such as stents, clamps, orthopedic implants, and many others are currently in use or are in development for medical purposes. The implants are inserted in the patient and are intended to perform a desired function over a given period of time, but are eliminated from the body without a further surgical procedure. The implants are therefore made of special absorbable alloys such as magnesium, iron, or zinc alloys, thus allowing the patient's body to degrade the implants over time so that ultimately they may be eliminated via the normal metabolism.

However, it is difficult to estimate the speed of the absorption process with sufficient accuracy, since this may vary from patient to patient. In clinical practice, however, it is important to know the state of degradation and the mechanical state (including the integrity) of the implants. Known methods such as X-ray, nuclear spin, ultrasound, intravascular ultrasound (IVUS), or optical coherence tomography (OCT) have only limited suitability for this purpose, since on account of the absence of spatial resolution and qualitative chemical selectivity they are not able to adequately image the transformation processes in the metal which sometimes occur at the microscopic and submicroscopic levels. Therefore, there is a need for a device which allows measurement of the state of degradation of absorbable metallic implants, and therefore of the proportion of the absorbed material and the mechanical integrity of the implants.

SUMMARY OF THE INVENTION

The invention introduces a measuring device including a sensor catheter, an evaluation unit, and means for receiving a magnetic field and converting the magnetic field to an electrical measurement signal which are situated in the sensor catheter and connected to the evaluation unit. The evaluation unit is designed to evaluate the electrical measurement signal.

In this simplest design of the measuring device, the magnetic field is generated outside the patient's body, and therefore separate from the measuring device, by an excitation coil, for example. In this manner use is made of the measuring device, designed as a catheter, to intracorporally measure the magnetic field in the vicinity of the implant.

The invention allows reliable detection of an absorbable metallic implant and determination of the quantity of the unabsorbed metallic material. For small implants embedded deeply in the tissue, the sensor catheter allows a minimally invasive procedure, although noninvasive use of the measuring device is also conceivable when the implant is placed near the skin surface and is large enough to be detected by measurement.

However, it is particularly preferred for the measuring device itself to contain means for generating the magnetic field, for example an alternating current generator and an excitation coil, situated in the sensor catheter and connected to the alternating current generator, for generating a magnetic field. The alternating current generator is designed to generate an alternating current and send same to the excitation coil for generation of the magnetic field.

The excitation coil placed in the sensor catheter may be introduced into the body together with the sensor catheter, and at that location generates a magnetic alternating field. The magnetic alternating field in turn generates eddy currents in a metallic body in the vicinity, and the eddy currents generate magnetic fields which counteract the magnetic alternating field of the excitation coil. The magnetic alternating field of the excitation coil thus becomes weaker the greater the quantity of metal that is present in the surroundings of the excitation coil, thus allowing the desired conclusion to drawn concerning the quantity and location of the remaining metallic material. Of course, the invention may also be used for localization and optionally for recovery of nonabsorbable metallic implants. In this case, quantitative information about the quantity of the metallic material is unimportant. It is also possible to detect cracks in a metallic implant, since the eddy currents are attenuated due to the nonconductive interruption in the metallic body, and the attenuation of the magnetic field of the excitation coil is less than would be expected for an intact metallic body. It is thus possible to perform a reliable integrity test of metallic implants.

In one preferred embodiment of the invention the alternating current generator is connected to the evaluation unit, and is designed to generate the alternating current at a frequency which may be specified by the evaluation unit in a frequency range between a lower limiting frequency and an upper limiting frequency.

This embodiment allows magnetic alternating fields to be generated at least one specifiable frequency. This takes into account the fact that bodily fluids, for example blood, may likewise be conductive due to the ions dissolved therein, so that here as well eddy currents having the above-described mechanisms of action are induced. However, in order to allow attenuation of the magnetic field of the excitation coil resulting from a metallic implant to be distinguished from that of blood, for example, it is helpful to be able to conduct the measurement at least one selectable frequency. At a high frequency, as a result of their mass and limited mobility the referenced ions in the blood experience little or no entrainment, whereas this is still possible for the freely mobile electrons in the metal. The measurement may thus be carried out taking the direct surroundings of the sensor catheter into account.

The lower limiting frequency is preferably between 5 kHz and 20 kHz. The upper limiting frequency is preferably between 1 MHz and 10 MHz. The alternating current generator is designed, for example, to generate frequencies in a range of 5 kHz to as high as 10 MHz.

Excitations are also possible which as the result of nonsinusoidal excitation (a rectangular signal or a burst signal, for example) cover multiple base frequencies in the relevant frequency range. Another alternative is for the device to automatically vary the frequency and adjust the measuring frequency to the specific measurement situation.

It is possible to select a measuring frequency such that the eddy currents are in resonance or near resonance with electrical or geometric characteristics of the implant. In other words, the measuring frequency may be made to be dependent on the natural frequency of the resonant circuits specified by the implant (implicit capacitive and inductive elements). It is thus also possible to obtain information concerning the total loss of mass of the implant on the one hand and the detachment of electrical connections (for example, struts for degradable stents), i.e., integrity, on the other hand, and to detect same in separate measured values.

In one particularly preferred embodiment variant the evaluation unit is designed to specify for the alternating current generator at a first measuring time a first frequency to be generated, and at a second measuring time, a second frequency to be generated which is different from the first frequency, and to evaluate the electrical measurement signal taking the first and second frequencies into account. If two or more measurements are made at respectively different frequencies, the above-described influence of interfering elements such as blood in the evaluation may be reduced or even eliminated. The second frequency is preferably at least five to ten times greater than the first frequency.

In one variant of the invention the evaluation unit is designed to determine a phase angle between the supplied alternating current and the electrical measurement signal. The above-mentioned attenuation of the magnetic field has an effect on the effective impedance of the system, which correspondingly influences the phase angle between the alternating current and the electrical measurement signal. The electrical measurement signal may accordingly be evaluated in the evaluation unit by measuring the phase angle between the alternating current and the electrical measurement signal.

Alternatively or additionally, the evaluation unit may be designed to determine the magnitude of the electrical measurement signal. Since, as previously described, the presence of a metallic body has an effect on the strength of the resulting magnetic field, the evaluation of the measurement signal may also be based on determination of this magnitude.

In one particularly preferred embodiment of the invention, the means for receiving the magnetic field and converting the magnetic field to an electrical measurement signal may be the excitation coil itself. In this case the evaluation is carried out by comparing the alternating current to the voltage over the coil, wherein the voltage over the coil represents the electrical measurement signal.

Alternatively, the means for receiving the magnetic field and converting the magnetic field to an electrical measurement signal may be a receiver coil. In this case the sensor catheter contains a pair of coils or a double coil. The evaluation is based on the voltage induced in the receiver coil by the magnetic field, the voltage in this case representing the electrical measurement signal.

In a further alternative embodiment, the means for receiving the magnetic field and converting the magnetic field to an electrical measurement signal may be a magnetic field sensor, in particular a Hall sensor or GMR sensor.

DESCRIPTION OF THE DRAWINGS

The invention is described based on the attached drawings.

DETAILED DESCRIPTION OF THE INVENTION

Figure 1:
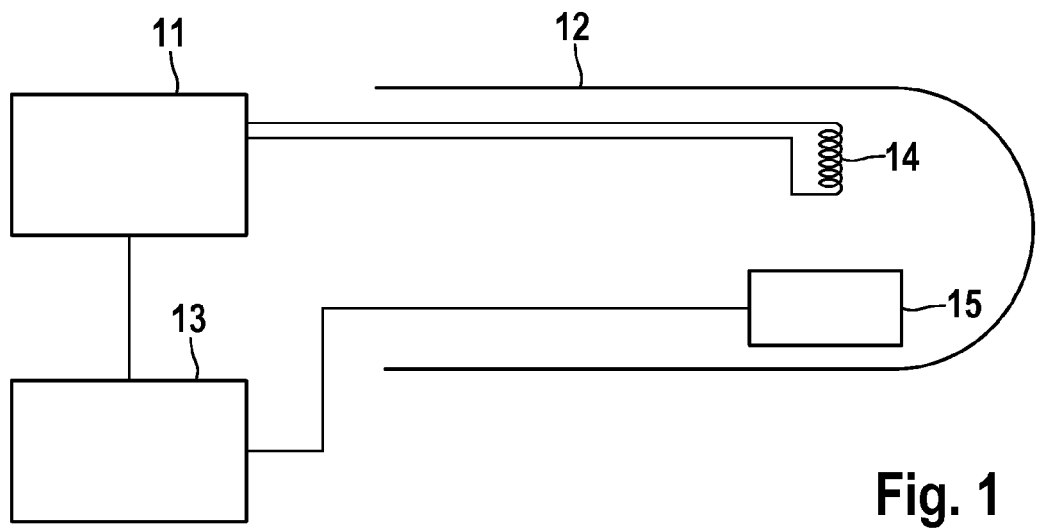
FIG. 1 is a block diagram of a measuring device according to the invention.

FIG. 1 shows a block diagram of a measuring device according to the invention. An excitation coil 14 for generating a magnetic field, and means 15 for receiving the magnetic field and converting the magnetic field to an electrical measurement signal are situated in a sensor catheter 12. The excitation coil 14 is connected to an alternating current generator 11 which is designed to generate an alternating current and send same to the excitation coil 14. In the illustrated example, the alternating current generator 11 is connected to an evaluation unit 13, which in turn is connected to the means 15 for receiving the magnetic field and converting the magnetic field to an electrical measurement signal. The evaluation unit 13 receives the electrical measurement signal from the means 15 for receiving the magnetic field and converting the magnetic field to the electrical measurement, and evaluates same. The evaluation unit 13 in the example is also designed to specify for the alternating current generator 11 a frequency of the alternating current to be generated by the alternating current generator 11. The electrical measurement signal may be measured by methods used in metal detectors for searching for buried metal objects (determination of the location and quantity of the metallic material) or for crack detection in metal pipes (integrity testing based on the attenuation of eddy currents as the result of nonconductive cracks).

Figure 2:
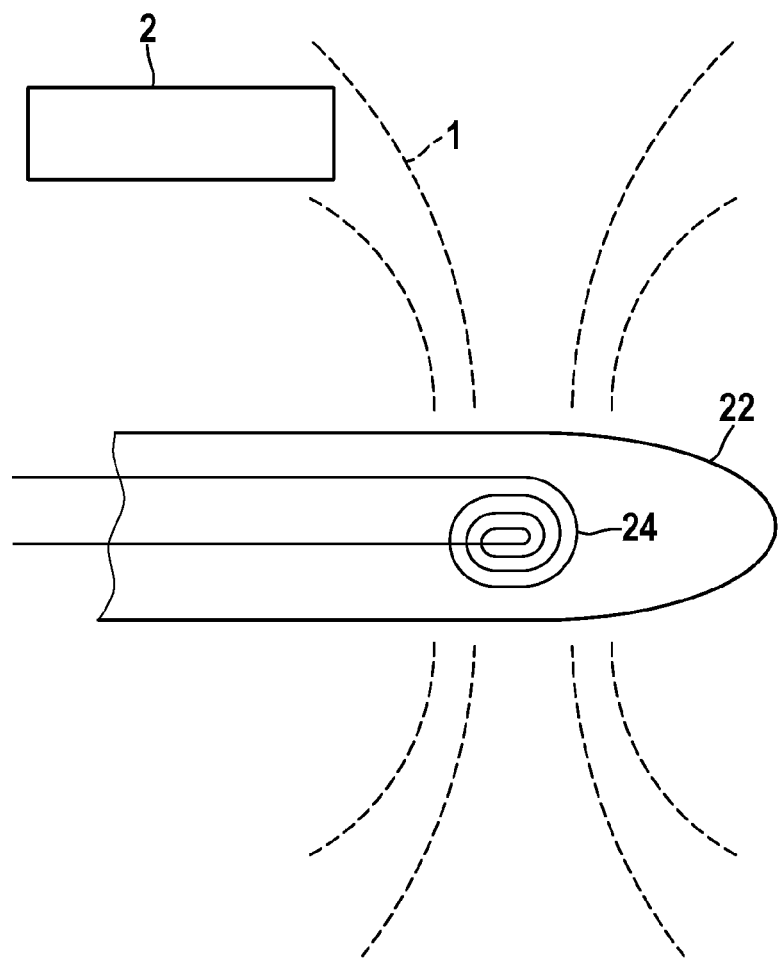
FIG. 2 is a cross section of the tip of a first embodiment of a sensor catheter.

FIG. 2 shows a cross section of the tip of a first embodiment of a sensor catheter 22. An excitation coil 24 which is designed to generate a magnetic field 1 is placed in the sensor catheter 22. However, the magnetic field 1, which in the following figures as well is indicated by dashed lines in the background of the figure for better illustration, also penetrates the sensor catheter 22. The excitation coil 24 may be designed as a planar coil produced by microsystem technology, and in the illustrated example functions both as a means for receiving the magnetic field and for converting the magnetic field to the electrical measurement signal. When an alternating current of suitable frequency is supplied to the excitation coil 24, the complex impedance Z thereof changes as a function of the presence of a highly conductive, for example metallic, body 2. The eddy currents induced in the conductive body 2 by the magnetic alternating field generate a magnetic alternating field which counteracts the magnetic alternating field 1 of the excitation coil 24, which is reflected by the impedance Z of the excitation coil 24. The evaluation unit, not shown in the figure, contains means for measuring complex impedance Z of the excitation coil 24 and for evaluating and optionally displaying or recording the measured values. The impedance measurement is preferably carried out at two or more different frequencies. The impedance measurements are evaluated with regard to the magnitude and phase of the complex impedance, using suitable known methods. The size and quantity of the highly conductive body or bodies 2, for example the residual quantity of an absorbable metallic stent in a blood vessel, may be determined in this manner.

Figure 3:
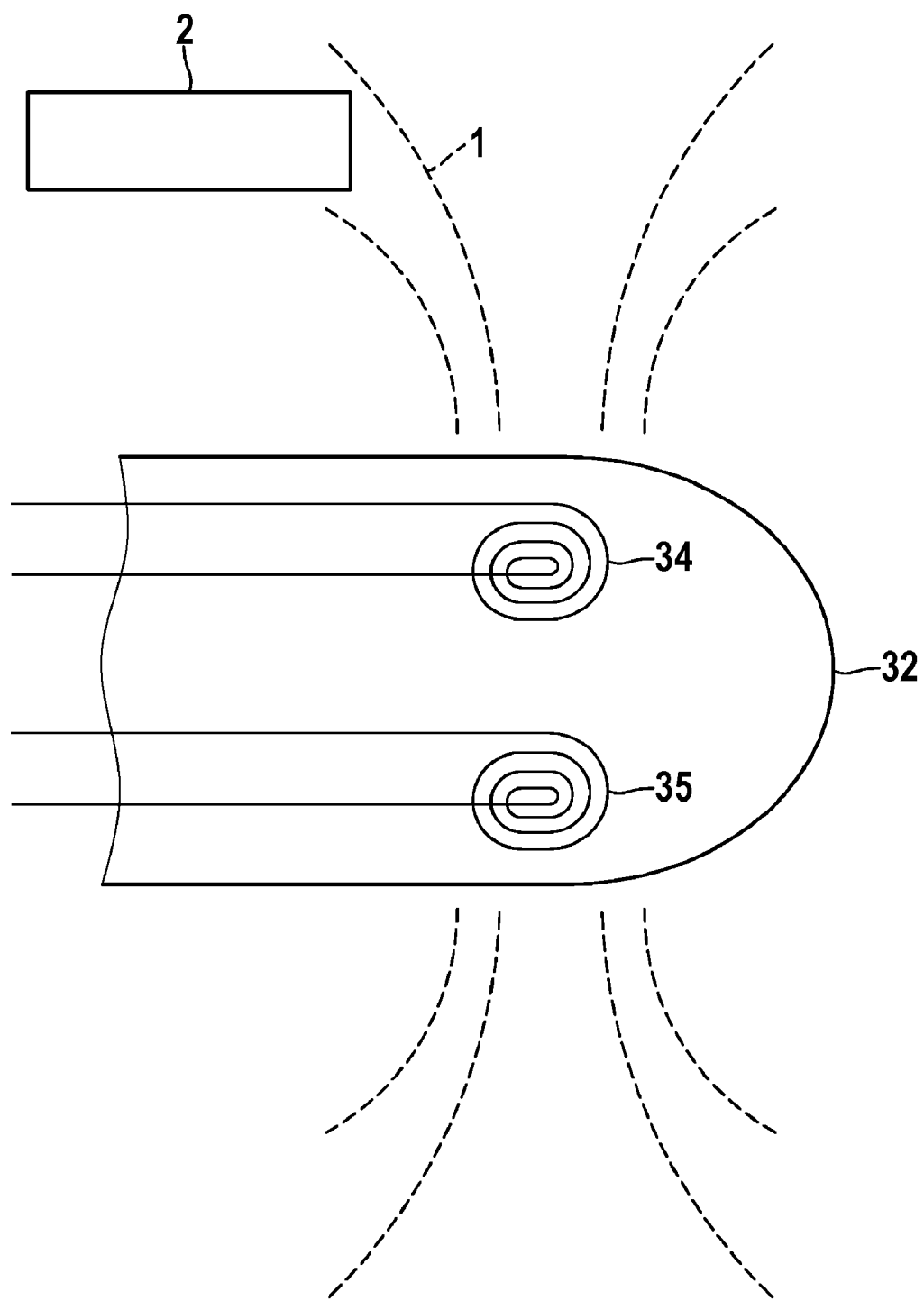
FIG. 3 is a cross section of the tip of a second embodiment of a sensor catheter.

FIG. 3 shows a cross section of the tip of a second embodiment of a sensor catheter 32. The system essentially corresponds to that of the first embodiment in FIG. 2, except that it has a pair of coils formed from an excitation coil 34 and a receiver coil 35. The magnetic field 1 generated by the excitation coil 34 generates by induction in the receiver coil 35 a corresponding electrical voltage in the form of an electrical measurement signal. Thus, in this embodiment the receiver coil performs the function of the means for receiving the magnetic field and converting the magnetic field to the electrical measurement signal. The magnetic field 1 is attenuated as a result of the previously described effects of a metallic body 2 present in the magnetic field 1, which is correspondingly reflected in the magnitude of the voltage induced in the receiver coil 35.

Figure 4:
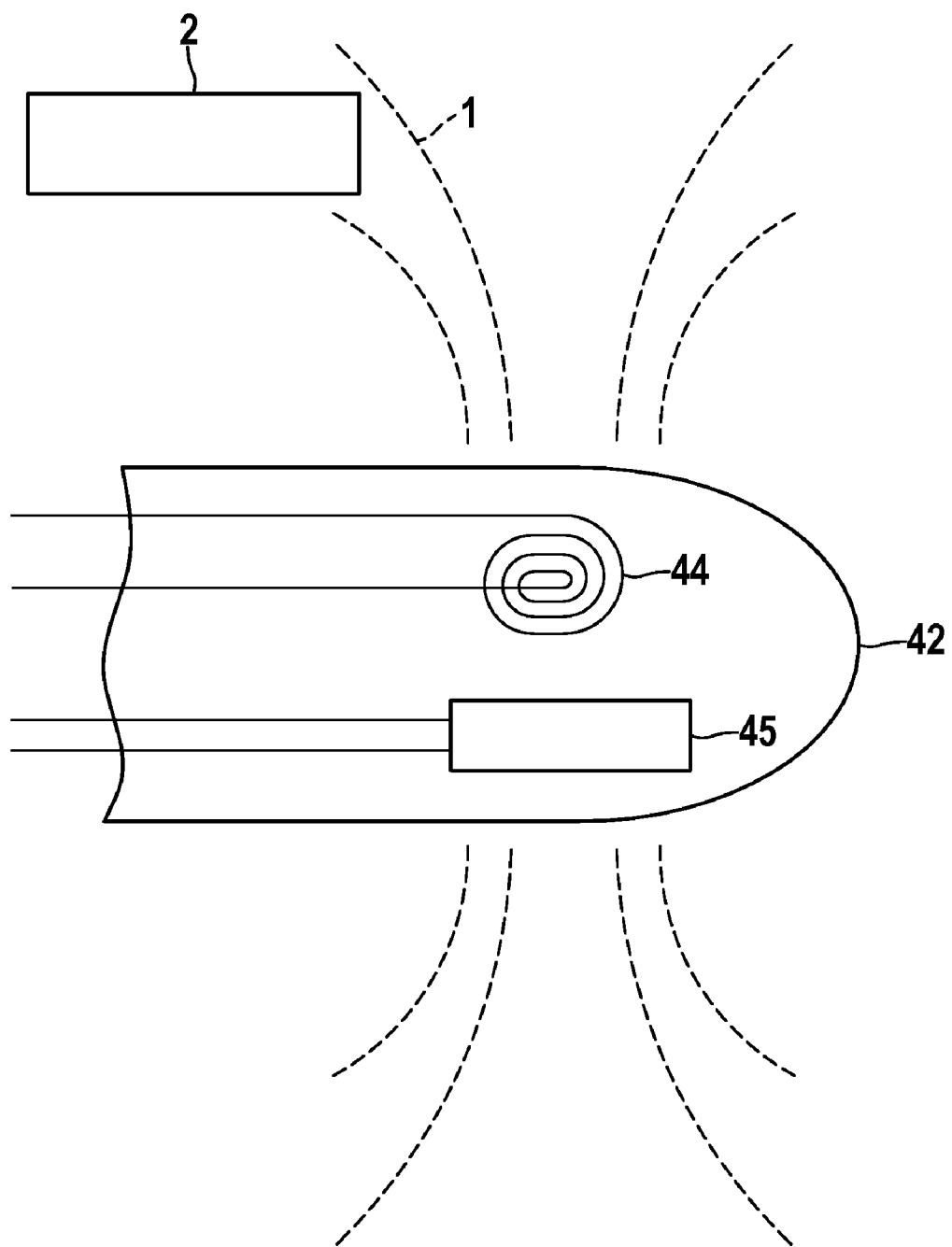
FIG. 4 is a cross section of the tip of a third embodiment of a sensor catheter.

FIG. 4 shows a cross section of the tip of a third embodiment of a sensor catheter 42. Once again the system essentially corresponds to the embodiments shown in FIGS. 2 and 3, except that it has a magnetic field sensor 45 which in this case performs the function of the means for receiving the magnetic field and converting the magnetic field to the electrical measurement signal. The magnetic field sensor 45 may be designed as a Hall sensor or a giant magneto resistance (GMR) sensor, for example. The excitation coil 44 and magnetic field sensor 45 may be implemented together in a single unit, using microsystem technology.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A measuring device comprising:
   a sensor catheter,
   an evaluation unit,
   an alternating current generator that generates an alternating current,
   an excitation coil situated in said sensor catheter and connected to said alternating current generator for receiving said alternating current and generating a magnetic field, and
   means for receiving a magnetic field and converting the magnetic field to an electrical measurement signal which are situated in said sensor catheter and connected to said evaluation unit, said evaluation unit being designed to evaluate said electrical measurement signal.

2. The measuring device of claim 1, wherein said alternating current generator is connected to said evaluation unit, and is designed to generate said alternating current at a frequency which may be specified by said evaluation unit in a frequency range between a lower limiting frequency and an upper limiting frequency.

3. The measuring device of claim 2, wherein said lower limiting frequency is between 5 kHz and 20 kHz.

4. The measuring device of claim 2, wherein said upper limiting frequency is between 1 MHz and 10 MHz.

5. The measuring device of claim 2, wherein said evaluation unit is designed to specify for said alternating current generator at a first measuring time a first frequency to be generated, and at a second measuring time, a second frequency to be generated which is different from the first frequency, and to evaluate said electrical measurement signal taking said first and second frequencies into account.

6. The measuring device of claim 1, wherein said evaluation unit is designed to determine a phase angle between said alternating current and said electrical measurement signal.

7. The measuring device of claim 1, wherein said evaluation unit is designed to determine the magnitude of said electrical measurement signal.

8. The measuring device of claim 1, wherein said means for receiving the magnetic field and converting said magnetic field to an electrical measurement signal is said excitation coil.

9. The measuring device of claim 1, wherein said means for receiving said magnetic field and converting said magnetic field to an electrical measurement signal is a receiver coil.

10. The measuring device of claim 1, wherein said means for receiving the magnetic field and converting said magnetic field to an electrical measurement signal is a magnetic field sensor.

11. The measuring device of claim 10, wherein said magnetic field sensor is a Hall sensor or a GMR sensor.

12. A method for determining the integrity of an implant comprising:
   providing the measuring device according to claim 1,
   introducing the sensor catheter into the body of a patient having an absorbable implant comprising a metallic material,
   using said excitation coil to generate a magnetic field,
   using said means for receiving a magnetic field to receive the magnetic field, and
   identifying changes in the magnetic field to determine the quantity and location of remaining metallic material of the implant.

* * * * *